(12) United States Patent
Torode et al.

(10) Patent No.: US 6,511,484 B2
(45) Date of Patent: Jan. 28, 2003

(54) TOOL AND SYSTEM FOR ALIGNING AND APPLYING FASTENER TO IMPLANTED ANCHOR

(75) Inventors: Ian Torode, Parkville (AU); John Cournoyer, Norfolk, MA (US); Carl G. Souza, Dighton, MA (US); Michael Varieur, Portsmouth, RI (US)

(73) Assignee: DePuy AcroMed, Inc., Raynham, MA (US)

( * ) Notice: Subject to any disclaimer, the term of this patent is extended or adjusted under 35 U.S.C. 154(b) by 0 days.

(21) Appl. No.: 09/896,826

(22) Filed: Jun. 29, 2001

(65) Prior Publication Data

US 2003/0004519 A1 Jan. 2, 2003

(51) Int. Cl.[7] ............................................... A61B 17/88
(52) U.S. Cl. ............................ 606/104; 606/99; 606/61
(58) Field of Search ..................... 606/104, 99, 100, 606/73, 61; 81/64, 44, 463, 450; 192/56.54; 227/175.1

(56) References Cited

U.S. PATENT DOCUMENTS

| | | | | |
|---|---|---|---|---|
| 5,499,986 A | * | 3/1996 | Dimarco | 606/104 |
| 5,720,751 A | * | 2/1998 | Jackson | 606/104 |
| 5,961,517 A | * | 10/1999 | Biedermann et al. | 606/104 |
| 6,132,435 A | * | 10/2000 | Young | 192/56.54 |

* cited by examiner

Primary Examiner—Pedro Philogene
(74) Attorney, Agent, or Firm—Nutter McClennen & Fish LLP

(57) ABSTRACT

A fastener cartridge installs clamping fasteners, e.g., a set screw and a lock nut, to fix a linking rod or cable in the head of an anchor assembly. The cartridge carries one or more fasteners, or pairs of inner and outer fasteners, and applies them onto the anchor head without cross-threading. A separate holder mechanism aligns and guides the cartridge with a centering body into which the fastener cartridge fits. One cartridge has a box wrench that externally grips and turns the nut, and a central shaft coaxial with the box wrench that positions and rotates a clamp screw in coordination with the nut. Preferably, these are configured, by springs, detents or offset positioning surfaces, to install the inner lock screw coaxially with but ahead of the outer nut to fix a linking member anchor assemblies prior to fitting, e.g., compressions and distractions of the spine and final tightening. The holder mechanism has a distal jaw that grips the anchor head and positions the centering body on-axis, aligning it to avoid cross-threading the fasteners. The holder may have an elongated handle projecting to a side of the centering body for manipulating the holder in a surgical wound, or the holder may have a coaxially disposed and/or telescopically interfitted handle. The handle also actuates a jaw to grip the anchor head and center the assembly. Fastener cartridges may be manually gripped or turned with a wrench remote from the wound. A floating assembly enhances alignment of threads and coordination of fasteners.

26 Claims, 17 Drawing Sheets

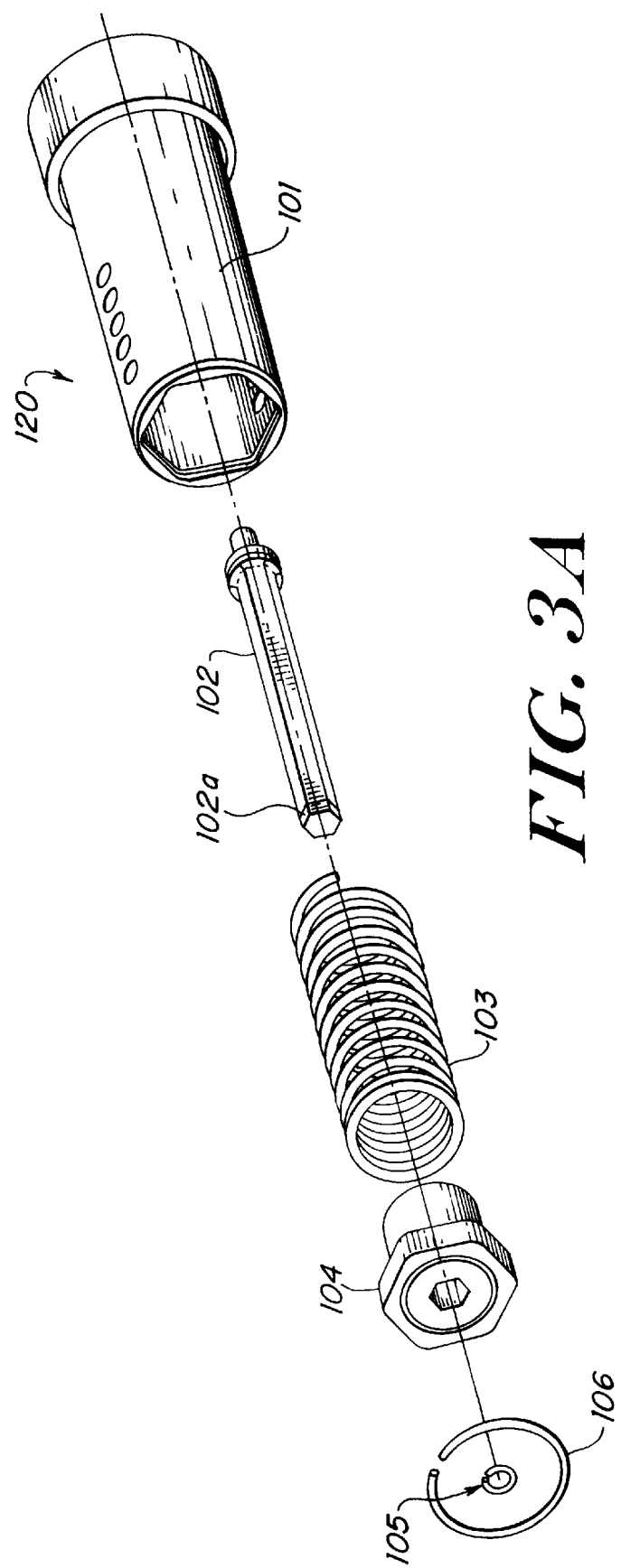

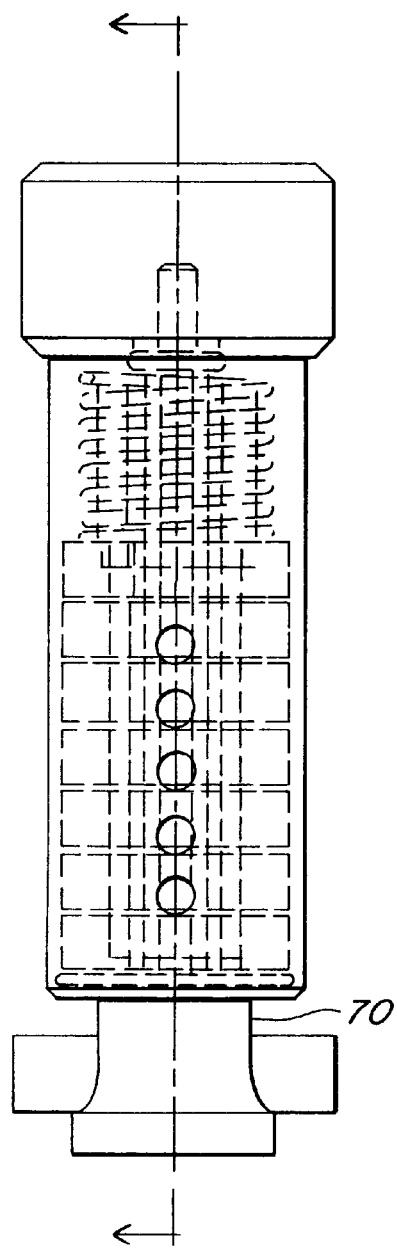
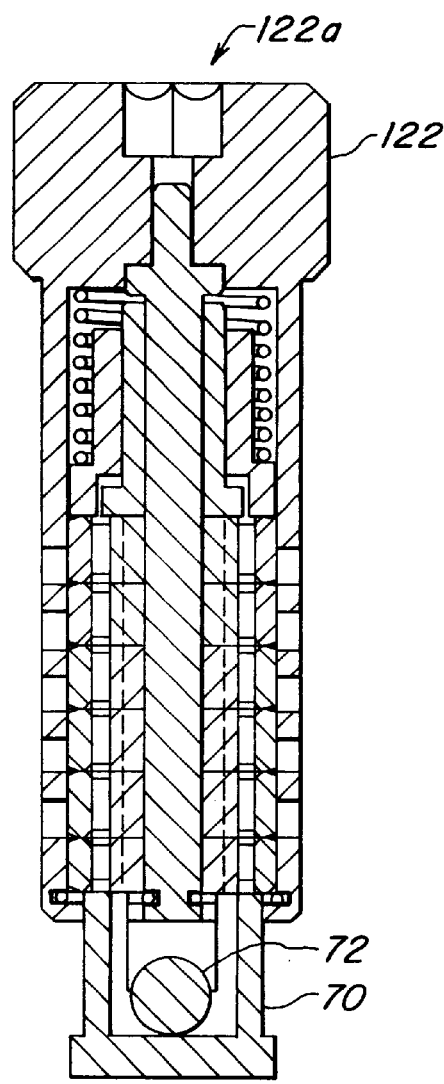
*FIG. 3B*    *FIG. 3C*

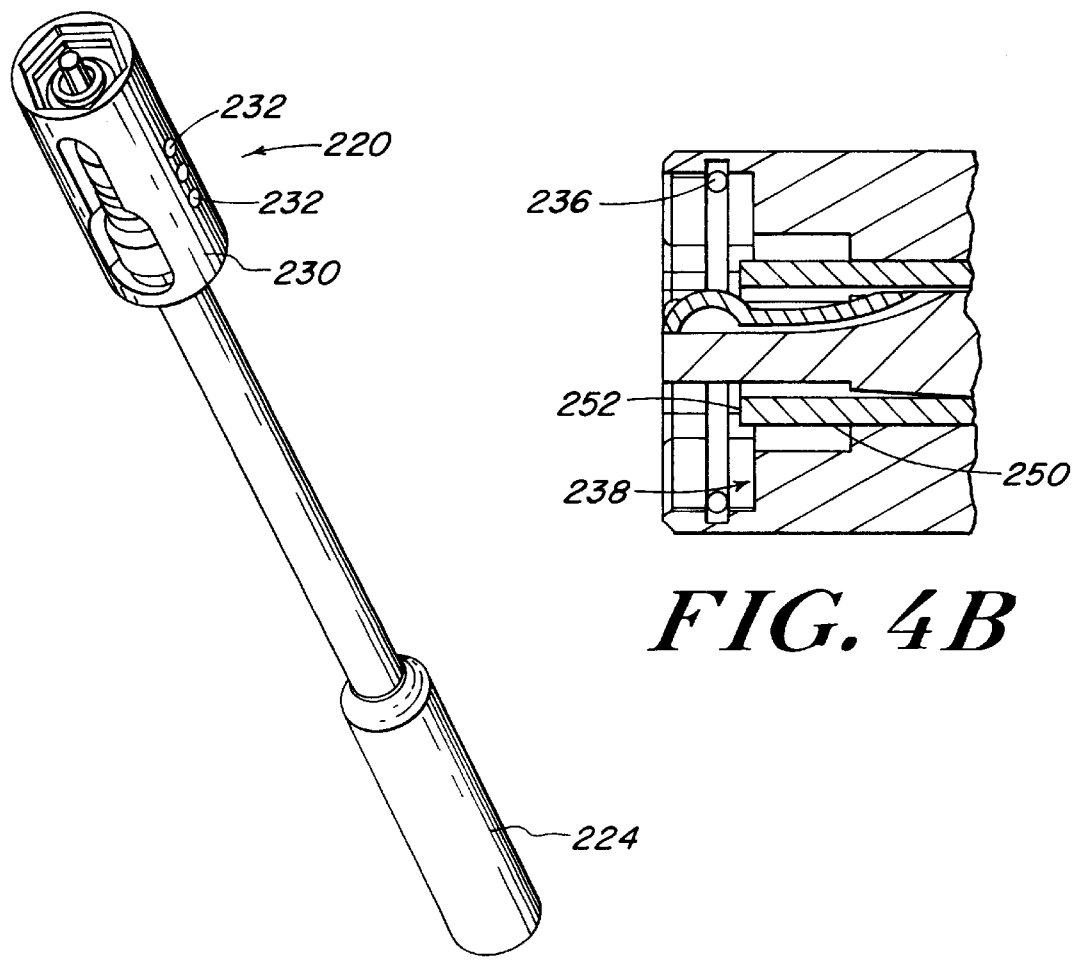
*FIG. 4B*
*FIG. 4A*
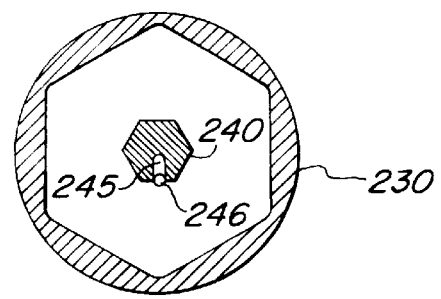
*FIG. 4C*

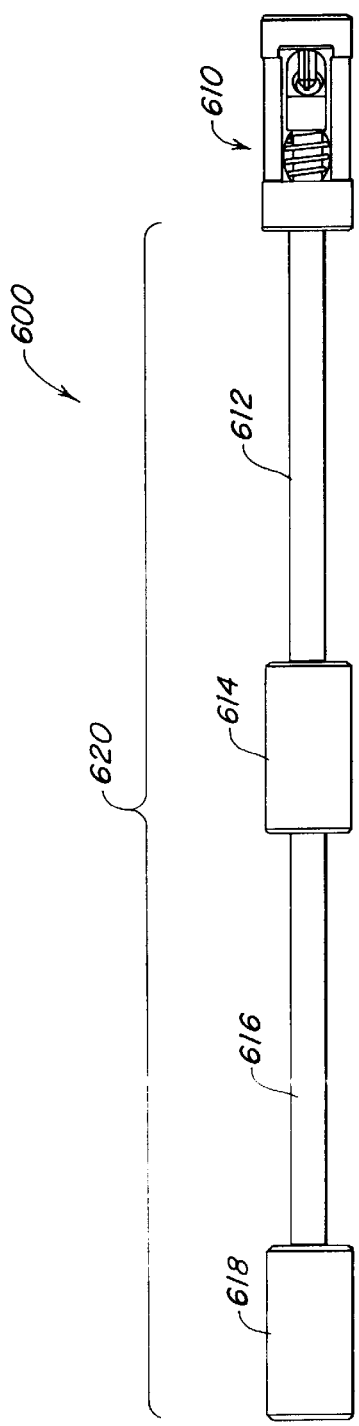
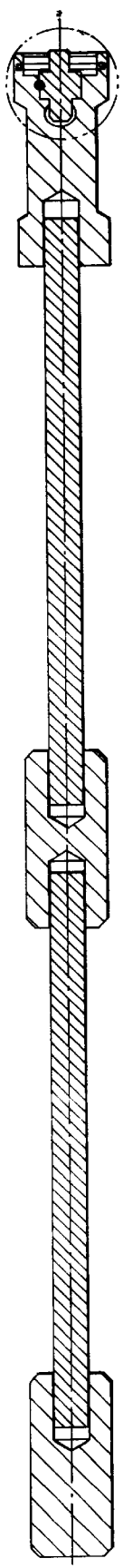
FIG. 6A
FIG. 6B

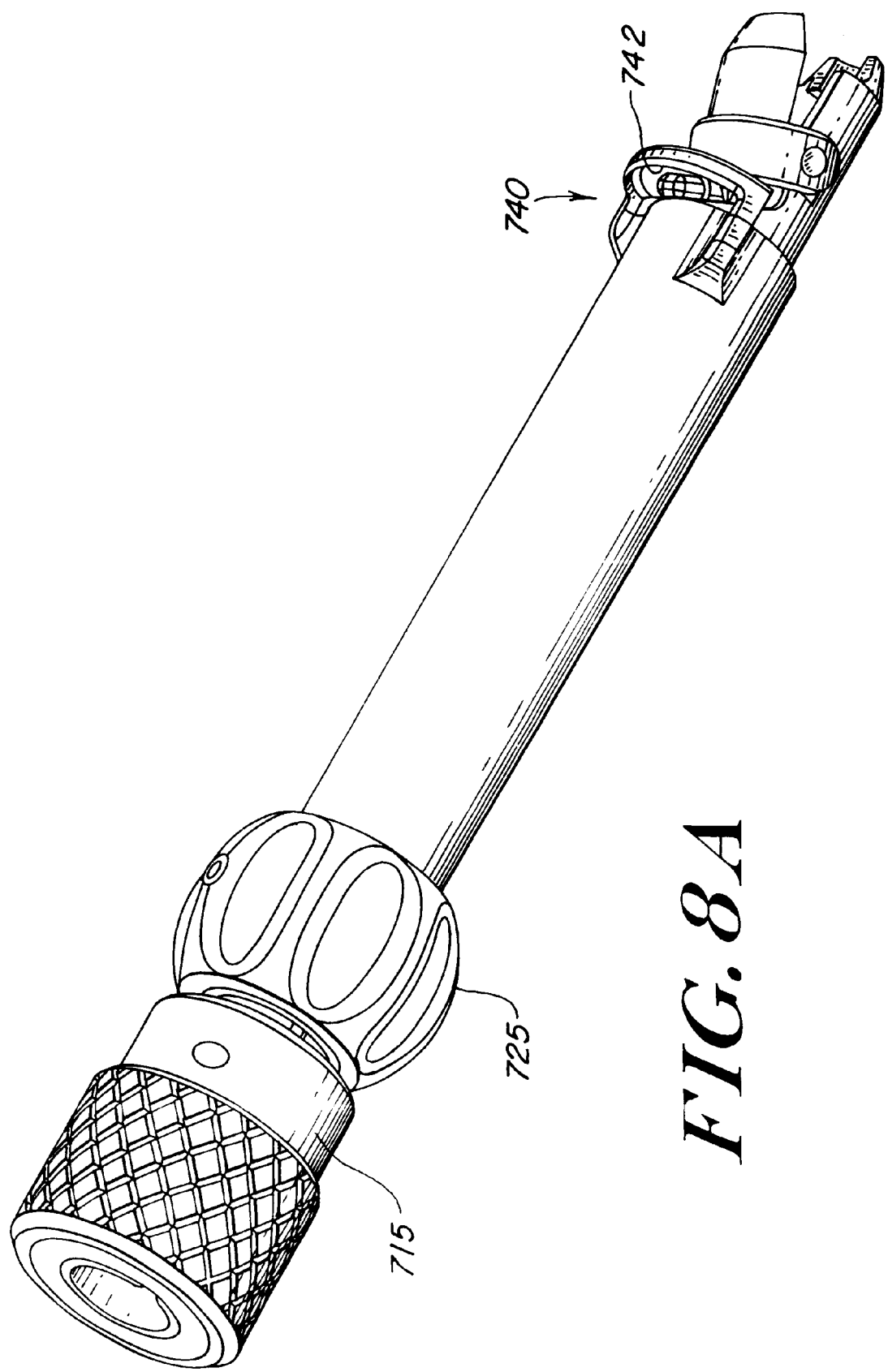

TOOL AND SYSTEM FOR ALIGNING AND APPLYING FASTENER TO IMPLANTED ANCHOR

BACKGROUND OF THE INVENTION

The present invention relates to tools for applying clamping fasteners, such as a lock screw and/or a lock nut, to a surgical implant, for example, to the head of a spinal anchor screw, or to a hook, to secure a linking member, such as a rod or cable. The linking member is also clamped to one or more other anchors, for example to stabilize or correct the spine.

A great number of such anchor bolt or screw assemblies are known. A typical procedure or operation may involve the placement of pedicle screws at various positions in hard tissue. Each screw directly or indirectly (e.g., via an offset plate) holds a head or cap structure into which the linking member fits to connect the anchor screw to other anchor screws situated remotely on adjacent vertebrae, and thereby operates to adjust or stabilize a region of the spine.

The anchor screw head or cap structure generally has a slot to accommodate the linking member, and has some mechanism for closing the top of the slot and clamping the rod or other linking member therein. Typically this is done in several stages, by first setting the linking member within the slotted head, for example capturing the connecting member with a cap or a lock screw that closes the receiving slot, and thus allowing the surgeon, in effect, to roughly align and/or contour the linking member; and then adjusting and effecting final clamping of the connecting member (e.g., with a lock nut or other fasteners).

Among the known constructions of this sort, one common construction provides the anchor screw with a slotted head that is internally threaded to receive an internal set screw, and the set screw is tightened down to initially fix the rod in place. The head may also be externally threaded such that a nut threaded about the outside provides additional circumferential strength, more forcefully clamps the rod, and firmly locks the internal set screw. Yet, other constructions involve a twist-on or slide-on cap that also accommodates a central set screw. The cap is first placed on the slotted head to capture the linking member, and the set screw is then tightened down. It is also possible to provide an external nut about the set screw to allow the set screw itself to be more firmly locked in such a cap member.

All such implanted anchor assemblies present the problem that the slotted head member must initially be open for receiving the connecting member, and the process of fitting or adjusting the rod requires tightening to be performed in several steps. Thus the process of capturing, adjusting and clamping the connecting member in the anchor assembly, which requires manipulation of several small components, presents a substantial risk that these components may be dropped or misplaced. Furthermore, the threading of one or more fasteners onto the anchor member, which often must be done deep in a wound, or at an unusual angle, with little room for manipulation, can be problematic and great care must be exercised to avoid cross-threading any of the fasteners.

It will be appreciated that during spinal surgeries utilizing a spinal rod system with pedicle screws and/or vertebral hooks, typically several compression and distraction techniques are carried out to compress or to distract the spinal column. A compression maneuver, for example, is done by positioning a compressor against two adjacent implants that are locked in place. The compressor is squeezed together. At the same time, the clamping fastener fixing the linking member to one of the implants is loosened, which allows the adjacent implants to be forced closer to each other along the rod. The fastener at that implant is then re-tightened. This maneuver results in incremental correction of the spine (i.e., it creates lordosis or kyphosis), and the surgeon may loosen and tighten the same implant several times before the spinal column is totally corrected.

One common set of hardware for such operations is the MOSS® Miami System sold by Depuy AcroMed, Inc., of Raynham, Mass., which utilizes an inner screw and an outer nut, thus a dual clamping mechanism, to secure a connecting member such as a rod to the implant e.g., anchor screw. The inner screw is typically set to temporarily lock the position of the implant on the rod during compression and distraction techniques. The inner screw achieves just enough force at low torque to lock the implant in place. If one were to use the outer nut, which is larger in diameter, it would clamp with greater force but would require the surgeon to exert a much higher torque to tighten and loosen the fasteners during the compression and distraction maneuvers. Generally, once suitable compressions and distractions have been carried out repositioning the anchor assemblies along the rod linking member, final tightening is effected by advancing the outer nut sufficiently so that it also contacts the connecting rod.

Typically these steps have required the use of several tools to install and tighten the clamping fasteners, e.g., the clamp screw and clamp nut. Moreover the process poses multiple risks of dropping or misplacing a fastener, or of misaligning (cross-threading) a fastener in the course of the multi-step procedure.

It would therefore be desirable to provide an enhanced tool for installing clamping fasteners on spinal implants and anchor assemblies.

SUMMARY OF THE INVENTION

One or more of these and other desirable ends are achieved in accordance with the present invention by a fastener cartridge that holds one or more threaded fastening elements and applies the element(s) to an anchor in alignment. The cartridge may simultaneously and coaxially hold both an inner and an outer threaded clamping fastener, coordinating the application of both elements, e.g., a set screw and a nut, to the head of an anchor screw. The cartridge has an outer wall forming a box wrench configured to both hold and turn the outer clamping fastener, while an inner shaft, having a cross sectional shape such as an Allen, star or other internal wrench, extending in the cartridge is configured to centrally hold and turn an inner fastener or set screw. A spring detent or other friction member may be arranged about the inner face of the outer wall to provide a holding force that gently retains the clamp nut therein. Another spring, detent or gripping element may be mounted on the central shaft to provide a similar holding force retaining the set screw on the central torquing shaft. In each case, the retaining force prevents the nut or screw from passively falling out of the cartridge, but allows it to advance as the cartridge turns during fastener installation.

In one embodiment, an axially offset central region is provided at the floor of the cartridge to position the inner clamp screw ahead of the outer clamp nut. This assures that the inner member is threaded onto the anchor head structure before the outer clamp nut, or starts threading a defined distance or number of threads before the nut advances. This central region may be spring loaded in an axial direction, allowing the set screw to float axially until its threads engage. In a method of use, when neither the inner and outer fasteners are initially matched with the starting thread of their opposed anchor, the cartridge may be rotated in a direction opposite the thread direction (e.g., counter clockwise) until the inner fastener drops into alignment, then turned clockwise to engage and advance the inner screw.

In further or other embodiments of the cartridge, the cartridge may have an elongated body that can be loaded with plural pairs of inner and outer clamp fasteners. In this case, the cartridge may include a spring-loaded pusher mechanism, and the fasteners may be loaded into a recess such that the pusher mechanism successively advances each pair of fasteners forward toward the distal face of the cartridge as the preceding pair is threaded onto an implant and leaves the cartridge. The cartridge itself, in either the single-pair or the multiple-pair embodiments, may be used as a stand-alone fastener applicator, for hand use without a separate holder or alignment jig.

Advantageously, the cartridge preferably has two knurled or other grippable surfaces. The distal surface (closer to the fastener end) permits more accurate manual alignment when applying a fastener to an implant in a shallow wound, reducing the risk of cross-threading due to angular misalignment between the central axes of the implant and the cartridge, and allowing axial rotation by fingertip manipulation. The cartridge may also possess an integral, on-axis handle extension shaft facilitating application of the clamping fasteners in deep wounds and allowing a screwdriver-like hand tightening.

Systems of the invention may further include a holder or alignment guide having a centering body with distal end jaws adapted to nest onto and circumferentially grip the head of the implant, and thus align the centering body with the body of the anchor screw or the axis of the head structure. In these systems, the fastener cartridge fits within the alignment guide, where it is turned by hand or with a tool, applying the fasteners concentrically without risk of cross-threading. The alignment guide may be used with cartridges that hold a single fastener or a concentric pair of fasteners, or cartridges that hold multiple fasteners or multiple concentric fastener pairs.

In one embodiment, the alignment guide includes an elongated handle projecting to a side of the centering body, allowing a surgeon to manipulate the centering body into position on the implanted anchor within the surgical wound while holding the handle assembly at an offset position outside of the surgical wound. In another embodiment, the alignment guide has an axially centered handle. This embodiment includes a substantially cylindrical centering guide that is telescopically interfitted with another substantially cylindrical member, and having an enlarged torque grip for handling. This embodiment allows the alignment guide to be positioned on-axis while held by a surgeon's hand sufficiently removed from the operative site. A second torque grip may be positioned closer to the fastener end to facilitate manipulation of the holder for actuating a clamping mechanism to align to and grip the anchor implant.

The alignment guide preferably includes distal end jaws which may be opened and then clamped about the head of the anchor assembly to effectively center the guide on the head such that the cartridge is held on-axis and does not cross-thread when rotated.

BRIEF DESCRIPTION OF THE DRAWINGS

These and other features of the invention will be understood from the description below, taken together with Figures which show illustrative embodiments and several variations and details of construction thereof, wherein:

FIGS. 3A to 3E show a cartridge configured to hold multiple pairs of inner and outer fasteners;

FIGS. 4A–4E illustrate one embodiment of a fastener cartridge with integral handle;

FIGS. 6A to 6E illustrate a multiple fastener installation cartridge embodiment of the invention;

FIGS. 8A–8C illustrate details of a practical implementation of the assembly of FIGS. 7A–7C.

DETAILED DESCRIPTION OF ILLUSTRATED EMBODIMENTS

The present invention provides a tool or set of tools for installing single or multiple fasteners, or pairs of fasteners, to capture or contain, and thus secure, a connecting member, such as a rod or cable, within an anchor head assembly, e.g., of an anchor screw, hook or the like. In presently preferred embodiments, inner and outer fasteners are installed in coordination by a single cartridge which holds both an inner and an outer fastener so as to enable them to be installed quickly and conveniently, without cross threading. Typically, the installed fasteners may then undergo appropriate tightening sequences during a fitting stage of a procedure, using final tightening instruments.

For purposes of illustration, representative embodiments will be described for an inner clamp screw having a central recessed cavity or wrench-receiving opening for torquing and turning the screw. That is, the inner clamping fastener element may be an Allen set screw or similar hardware fastener. The outer clamp fastener may be a threaded nut, such as a six-, eight- or twelve-sided nut, and most typically a hexagonal nut.

As noted above, prior art assembly of these fasteners in spinal surgery involves capturing the rod in an anchor slot, loosely inserting the inner screw, and loosely threading on the outer nut, which is then typically followed by provisionally tightening the inner screw to lock the rod in place at the anchor assembly (with a final tightening tool). During a procedure, the surgeon proceeds to compress or distract the spine before performing final tightening of the outer nut. This procedure may be repeated for a number of anchor points.

Figure 1A:
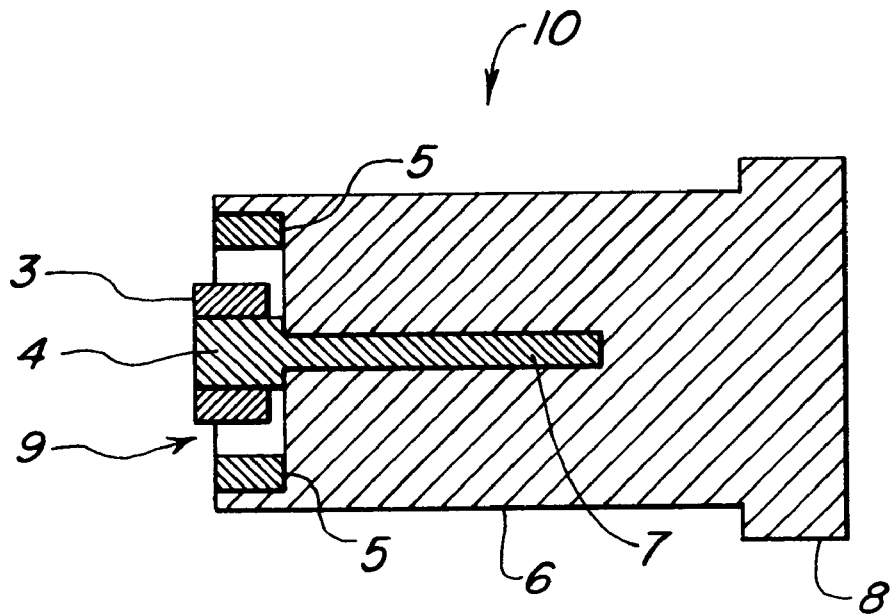
FIGS. 1A–1B show a fastener cartridge for applying a pair of fasteners to an implanted anchor in accordance with the present invention.

The present invention simplifies and coordinates the manipulation of the clamping fasteners for their initial application to the anchor point (e.g., to the anchor screw, hook or other anchor assembly) by providing a cartridge, one example of which is shown in FIG. 1A. As shown, the cartridge 10 has a cartridge body 6 with an enlarged gripping portion 8 at its proximal end and a wrench portion at the other, distal, end 9. The wrench portion includes a socket or recess 2 having a polygonal shape for accepting the fastener nut, thus forming a box wrench for turning the nut. The distal end 9 also includes a centrally-protruding shaft or driver 4 which, as discussed above, is preferably an Allen wrench (i.e., a hexagonal plug wrench) or other driver for seating in the socket of, and driving a set screw. For purposes of illustration, an set screw 3 and an outer nut 5 are shown in the cartridge.

Thus, the distal end of the cartridge 10 accommodates two threaded fastening clamp elements at once. Advantageously, in this embodiment the inner driver element 4 extends ahead of the outer socket element 2 so as to preferentially and coaxially install the inner set screw before or somewhat ahead of the outer nut.

The inner driver 4 may take the form of a separate short driver shaft that is threaded at one end 7 and rigidly screwed into the cartridge body 10 to rigidly turn when the outer body is turned. Alternatively, the central part of the body 10 may be hollow and the inner driver 4 may be implemented as a long shaft that extends past the proximal end of the cartridge; or it may terminate with its own drive plug or socket that couples to a corresponding proximal end shaft (not illustrated) or to an external wrench that may be in a remote position outside the wound.

Figure 1B:
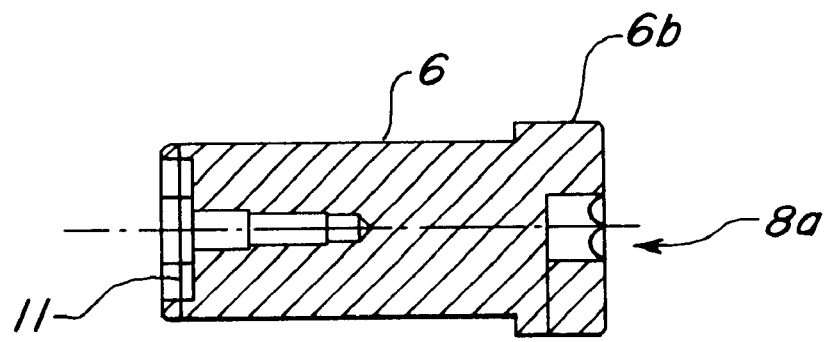

FIG. 1B illustrates a cross sectional view through the cartridge 10 of FIG. 1A with the driver 4 removed. As shown, a hex driver socket 8a is provided at the proximal end 6b of the body 6. The proximal end of the cartridge also has an enlarged outer surface, which is preferably also knurled, corrugated or otherwise shaped, to enhance gripping. At the distal end, an internal circle clip 11 is placed slightly recessed from the end face in the hexagonal socket wrench recess 2 to more securely grip and hold a nut therein while allowing the nut to pull out by sliding motion as it is threaded onto the anchor screw. By way of scale, the outer nut may be a hexagonal nut having a dimension typically of about 8.5 to 15 millimeters across flats, while the inner driver may be a 2.5–6 millimeter hexagonal driver that fits a set screw of about 8 or 10 millimeters diameter. The circle clip 11 may be set in a groove recessed approximately one millimeter from the distal end of the cartridge, while the hexagonal recess may extend to a floor or protruding shelf on its inner wall several millimeters beyond that which serves to limit the depth of seating of the nut in the socket.

Figure 2A:
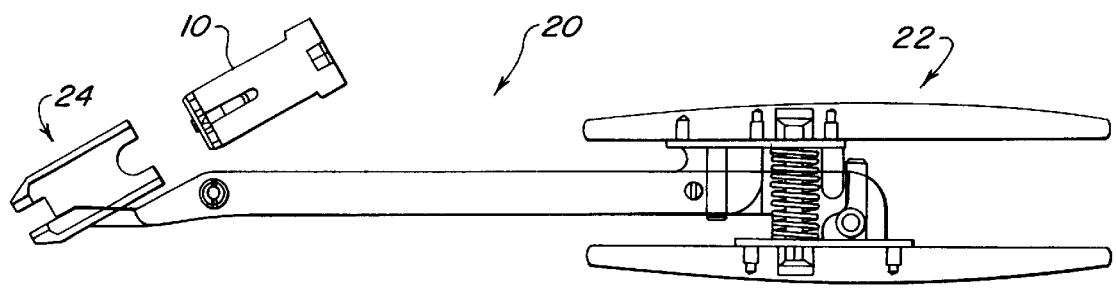
FIGS. 2A and 2B show a cartridge holder, for use with the cartridge of FIGS. 1A–1B.

In accordance with another aspect of the invention, an alignment guide or holder 20 is provided for the cartridge. The fastener applying cartridge 10 fits within and is aligned by the holder device 20. One embodiment of such a holder is shown in FIG. 2A. The holder device 20 has a handle portion 22 and an alignment portion 24. The alignment portion includes a jaw-like mechanism 24a, 24b controlled by the handle 22 that opens up, and closes down upon the head of an anchor screw to precisely grip the head and simultaneously bring the holder in axial alignment with the anchor screw. The alignment portion also has a cylindrical body with a bore within which the cartridge 10 may rotate. This assures that the fastening clamp elements carried by the cartridge will be aligned on axis so that they do not cross-thread. As shown, the alignment portion 24 closes down to form a substantially cylindrical sheath within which the cartridge 10 rotates freely.

When so used with the alignment tool 20, the cartridge 10 need not be rotated by hand but may be driven via its proximal end Allen socket 8a. This permits the cartridge to be smoothly and accurately torqued. By using a ball-end Allen wrench (not shown), torque may be applied either from an on-axis or from an off-axis position. The illustrated holder device has a pliers-like mechanism for closing the jaws on the head of the anchor screw, and has a spring loaded handle 22 which allows the device to be set in position, and to be released and reopened, by minimal and convenient manipulation with one hand.

Figure 2B:
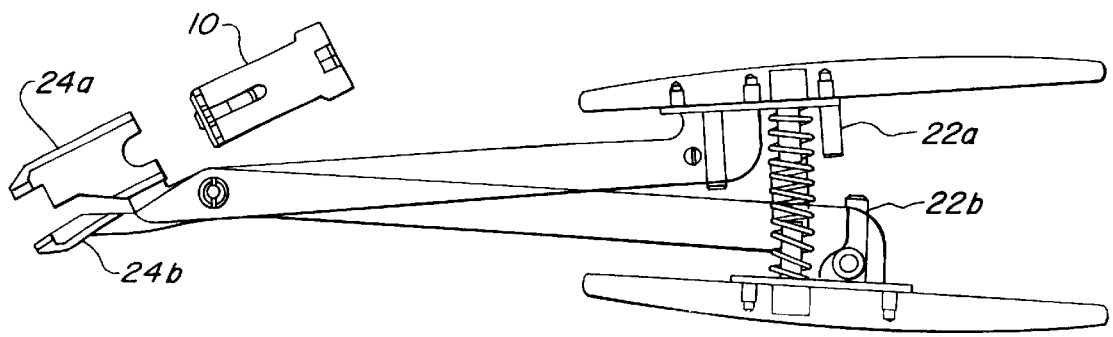

The holder assembly 20 has a handle with spring biased grips at the holding end 22 that, as illustrated, carry opposed ratchet catches 22a and 22b to lock the handle closed with the jaws 24a, 24b firmly gripping the head of an anchor assembly. As further shown in FIG. 2B, the handle portions rock slightly so that depending on what portion of the handle is depressed, the handle either locks or unlocks the jaws. Pressing the top proximal portion rocks the ratchet locks 23a, 23b apart, releasing the handle from a locked position. This allows a surgeon to hold the handle of the holder with one hand and to insert the fastener cartridge with the other hand. Once the inner screw and the outer nut are placed onto the implant, and the cartridge is removed, the surgeon can slide his hand upward (proximally) and simply press the handle together to unlock the jaws. The jaws of the holder end 24 open wide enough so that they do not catch on the external nut as the holder is removed from the head of the anchor prosthesis.

In accordance with another aspect of the invention, a cartridge 120 may alternatively be configured as shown in FIGS. 3A to 3E to hold multiple pairs of inner screws and outer nuts. This embodiment has the advantage that the cartridge itself is elongated, and provides an enhanced gripping area that may be hand-held for torquing the fasteners dispensed by the cartridge. The cartridge body may be made of a lightweight material (e.g., a polymer) and may be configured as a relatively simple and inexpensive article of manufacture, which may be disposed of after dispensing the clamp fastening elements. The cartridge is also suitably implemented in an all-metal, autoclavable construction intended to be refilled and re-used.

As shown in the exploded perspective view of FIG. 3A, the multi-fastener cartridge 120 includes an outer body 101 of generally cylindrical outer contour with a inner bore 101a shaped to receive the fastening nut, e.g., a polygonal inner bore, with a representative cross-flat dimension of about 8.5–15 millimeters appropriate for the intended fasteners. An elongated drive shaft 102 of hexagonal cross section fits centrally in the outer body 101 and is centered by an end wall (not visible in the Figure) that closes the proximal end of the outer body. A spring 103 and a plunger body 104 fit about the drive shaft 102 such that the plunger body 104 rides on the drive shaft 102 and is biased toward the distal end of the body. The plunger is retained on the shaft by an external circle clip 105 that fits in a groove 102a near the distal tip of the shaft 102. An internal circle clip 106 fits in a groove formed in the hexagonal inner bore of the body 101 near to the distal end. This clip functions to frictionally retain a fastening nut loaded into the cartridge 120 as described for clip 11 of FIG. 1A. In this multi-fastener cartridge, the above-mentioned circle-clips or other frictional retaining elements (such as a compressible rubber seat) serve to retain the front screw/nut at the face. A mechanism such as a pawl stop or detent may be provided to act on the fasteners below the front rank and prevent the spring mechanism 103, 104 from prematurely ejecting fasteners. Other mechanisms may also be employed if necessary to successively advance the fasteners, or to tailor (increase or limit) the level of force exerted by the fastener feed system.

Figure 3D:
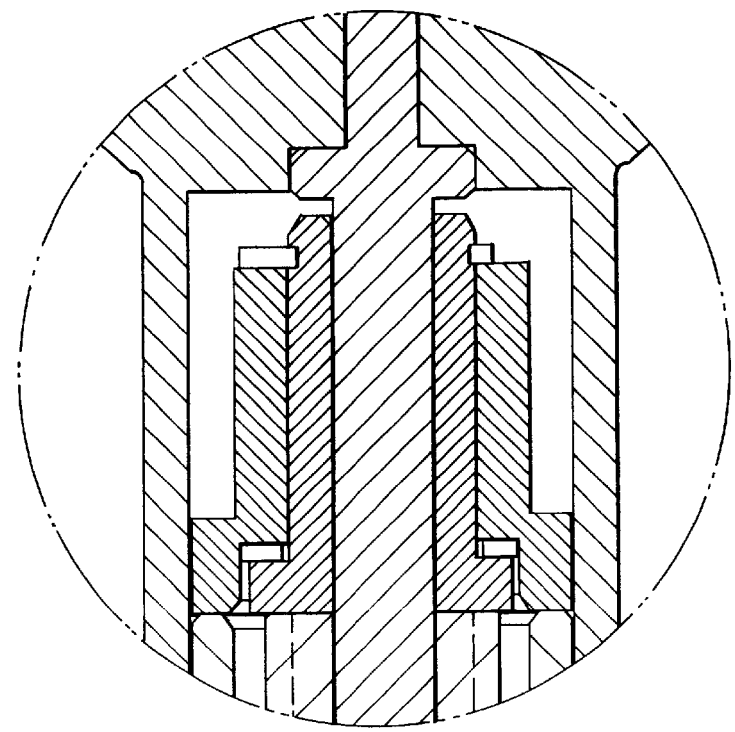
Figure 3E:
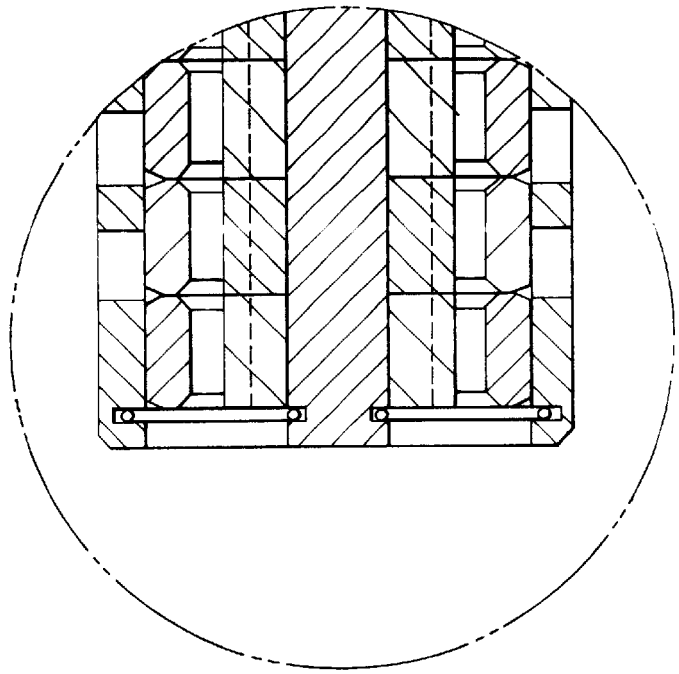

FIG. 3B illustrates the cartridge 120, with its inner spring advance assembly shown in phantom, loaded with plural pairs of fasteners, and FIG. 3C shows cross section taken along a diametral plane of the cartridge. The cartridge is shown seated on the slotted head assembly 70 of an anchor screw, above a linking rod 72 captured therein. As shown, the drive shaft 102 extends to the threaded bore of the anchor head 70, and the spring 103 urges the front set screw axially into engagement with the anchor head. The cartridge has an enlarged hand grip 122, with a drive recess 122a that allows the cartridge to be turned from outside the wound. FIGS. 3D and 3E illustrate greatly enlarged detail views of the proximal and distal ends, respectively, of the cross section of FIG. 3C.

Another embodiment of the invention may be implemented as a spring loaded cartridge that holds a single pair (inner and outer) of clamp fasteners and is integrally connected with a driver. FIGS. 4A–4C illustrate one embodiment of this device. As shown in FIG. 4A, the device includes a spring loaded cartridge portion 220 and a handle driver portion 224 forming an integral long rod-like assembly. As best seen in the end view of FIG. 4C, the cartridge portion 220 includes an external body 230 that acts as a hexagonal box wrench for gripping the lock nut, and an internal driver 240 shaped to drive a set screw. Driver 240 is a hex driver with a slotted groove 241 into which a spring 246 is fitted. Spring 246 is biased outwardly so that the internal driver 240 firmly grips the set screw when mounted on its tip. In practice, a set screw lying on a flat table may be simply picked up by the cartridge 220 by pressing the driver down against the set screw.

FIG. 4B is a cross sectional view through the device of FIG. 4A in the plane of the driver slot 245, showing more detailed construction of the driver/wrench elements. As shown, a central cylindrical bushing rides along the shaft of the driver 240. The box wrench recess in the outer portion 230 has a seat situated at a shallow depth so that when a clamp nut is loaded into the cartridge, it resides essentially at the end face of the cartridge. As with the earlier described embodiment, a circle clip 236 frictionally engages the outer nut to hold it centered in position. A spring such as a Belleville washer (not shown) or a coil spring 238 (FIGS. 4A,4B) allows the cylindrical bushing 250 and set screw fastener to move backwardly on the central driver shaft a small extent as the clamp fasteners seat. This greatly enhances the ability of the tool to apply the fasteners without cross-threading. In a typical installation procedure, if a fastener has not started to thread, the cartridge may be rotated counter-clockwise (opposite the thread sense) with slight axial pressure until the surgeon feels the fastener drop into engagement indicating that the starting threads have lined up, and then turned clockwise to apply the fastener. As shown in FIG. 4B, the central bushing 250 extends slightly forward of the floor 238 of the box wrench opening, forming a raised protruding seat 252 that positions the set screw held on the driver 240 to be ahead of the lock nut held in the box wrench. This assures that the set screw is generally advanced and threads ahead of the lock nut, leaving the lock nut backed off during initial compression/distraction fitting steps.

The single unit design of FIGS. 4A–4C is also adaptable to a multi-unit cartridge that holds a stack of set screw/ locknut fastener pairs in a manner similar to cartridge 120 of FIG. 3, with a mechanism providing a suitable floating spring-loaded stack in the external torquing shell 230. In each of the cartridge embodiments described so far, when the cartridge is formed of a metal and intended to be reused and sterilized, the cartridge preferably includes a plurality of holes or openings 232 (FIG. 4A) communicating between outer portions of the device and inner portions of the assembly. These allow steam, fluid or reactive gas to more readily access all portions of the device so that it may be dependably autoclaved or sterilized. Such holes or openings may also be provided in disposable polymer embodiments of the cartridge, although suitable sterility in a single use device can also be achieved by other means not requiring physical access, such as by gamma ray or other radiation sterilization techniques, without necessarily requiring additional apertures or similar design modifications.

Figure 4D:
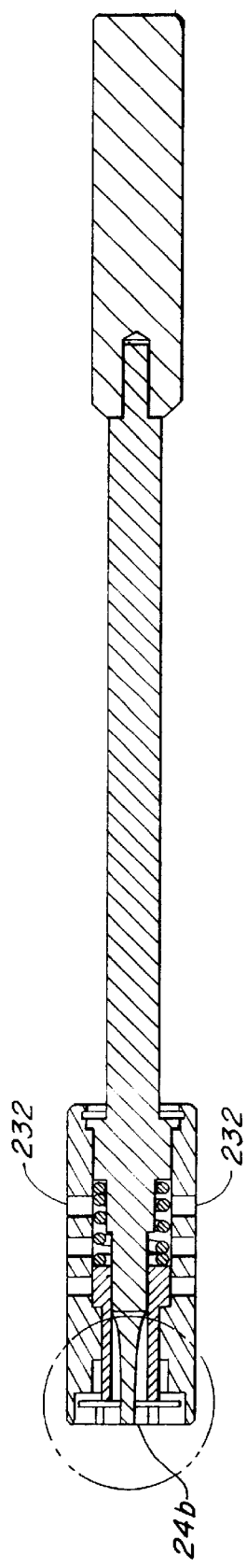
Figure 4E:
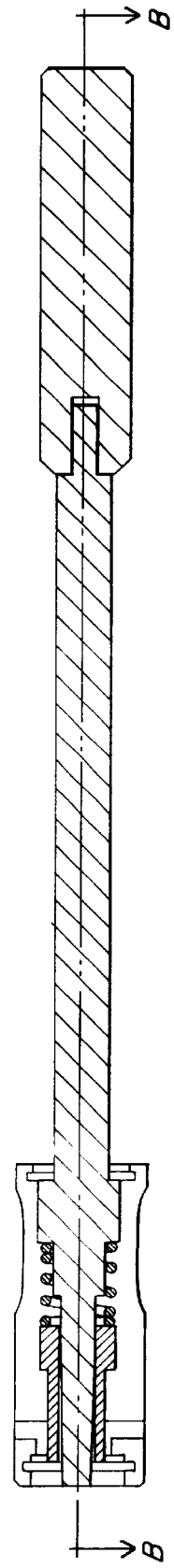

FIGS. 4D and 4E illustrate sections along two orthogonal planes passing through the axis of the tool of FIGS. 4A–4C. As shown in FIG. 4D, the retaining spring 246 (FIG. 4C) seats centrally in a groove formed in one face of the central hexagonal driver. Also, the apertures 232 provide through passages through the outer shell on both sides of the body in addition to the larger keyhole-shaped aperture visible in the perspective view of FIG. 4A. As shown in these cross sectional views, the central driver is integral with the handle rather than a separable element. However, in other embodiments, the fastener dispensing cartridge-like distal end 220 may be formed as a separate cartridge with its central shaft only extending as far as the proximal end of the outer body, and may have a recessed socket formed therein so that it may be turned with a rigid straight or ball-head Allen wrench.

Figure 5A:
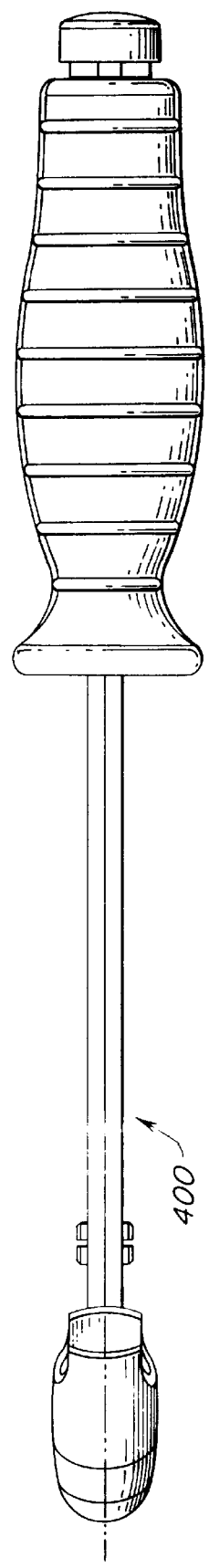
FIGS. 5A to 5C show views of another embodiment of a holding/alignment tool.
Figure 5B:
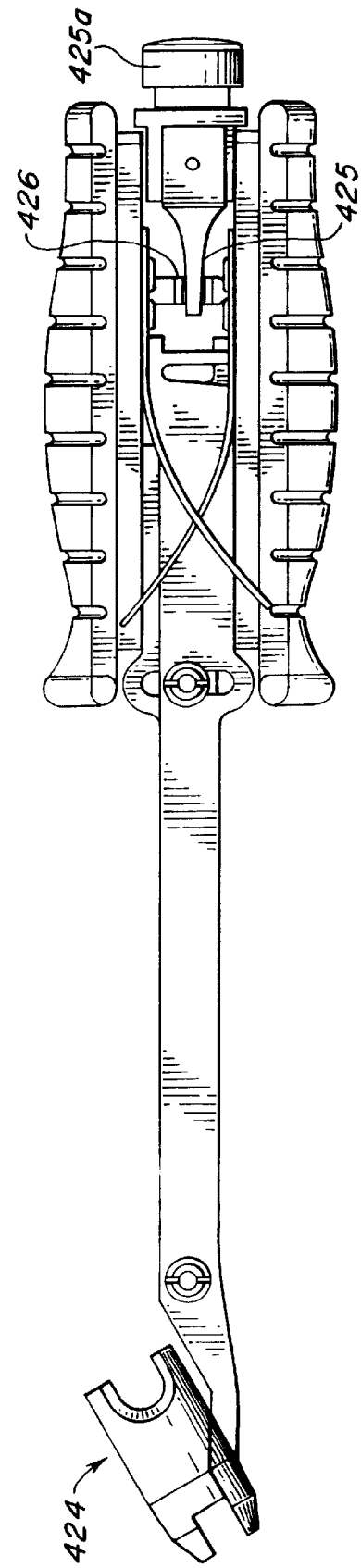
Figure 5C:
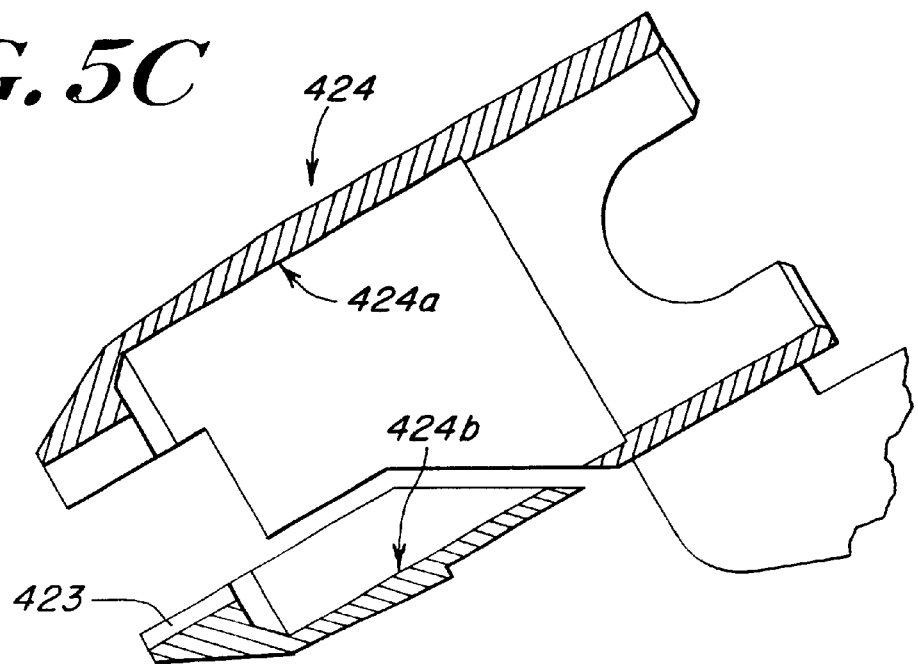

FIGS. 5A and 5B show top and side plan views respectively of another holding/alignment tool 400 useful with any of the cartridges described above. As with the previously described holder/alignment tools, tool 400 includes gripping assembly 424 formed as a set of jaws for gripping an anchor screw head, and a handle assembly 422 configured to close the jaws and lock them in a closed position. FIG. 5C is a cross sectional view showing the profile of the inner edges of the jaw assembly, which is effective for reaching around and locking onto the head of an anchor screw in such manner as to exactly align the cylindrical holder body with the axis of the anchor head. As shown, each segment of cylindrical jaw, portion 424a, 424b, includes a radially inward hooked lower lip 423 that seats below and cylindrically centers the jaws on the anchor screw head. At the handle end, the alignment tool 400 further has a toothed prong 426 that is captured by a hook or catch, 425 allowing a simpler more secure method of operation wherein the catch 425 quickly catches or releases the toothed member 426 without necessitating any rocking motion of the handle itself, and without requiring the more complex suspension structure of the previously described embodiment. This form of catch prevents inadvertent release of the jaws, and the hook 425 may be spring biased back, so that by pushing on button end 425a the catch 426 is released. One or more flex springs may bias the handle open.

In accordance with another aspect of the present invention, the fastening system of the invention may include a cartridge similar to the single pair or multiple pair fastener cartridges described above, and having an integral torquing handle extending from the proximal end of the cartridge along the installation axis. This embodiment may include additional grip portions located along the length of the proximal end.

FIGS. 6A to 6E illustrate one embodiment of a fastener installation tool according to this aspect of the invention.

As shown, installation tool 600 comprises a fastener holding cartridge 610 integral with a handle assembly 620 for turning the cartridge as the fasteners are installed. The handle assembly comprises a distal shaft 612 that extends from the cartridge 610 to a mid grip 614. The handle further includes a proximal shaft 616 extending from the mid-grip to a proximal hand grip 618. The handle portion may, for example, be about eight inches long, adapting the tool for use in deep wounds. The mid grip 614 provides enhanced control that allows a surgeon to more easily hold the entire handle accurately aligned along the axis of the screw to avoid cross threading. FIG. 6B shows the tool of FIG. 6A in cross section. The cartridge 610 is illustrated as a simple cartridge holding a single pair of fasteners at its distal tip, and the central drive shaft is implemented with a small stub insert 630 that is positioned to hold and drive a set screw.

Figure 6E:
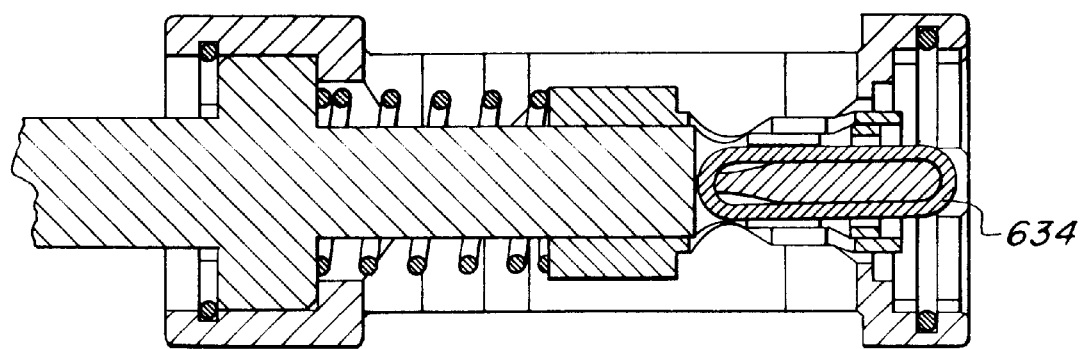
Figure 6C:
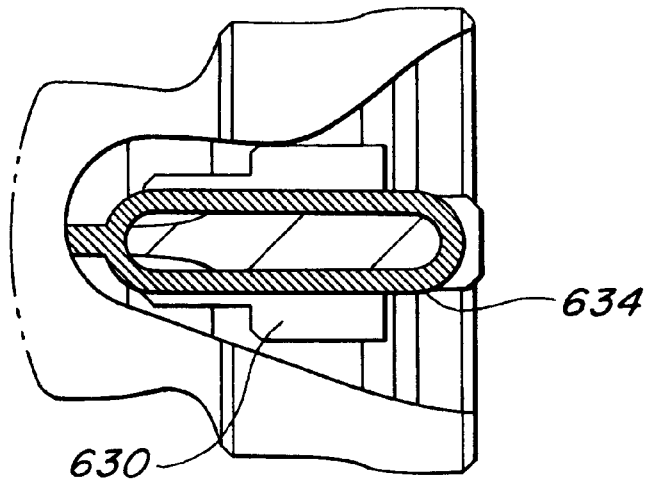
Figure 6D:
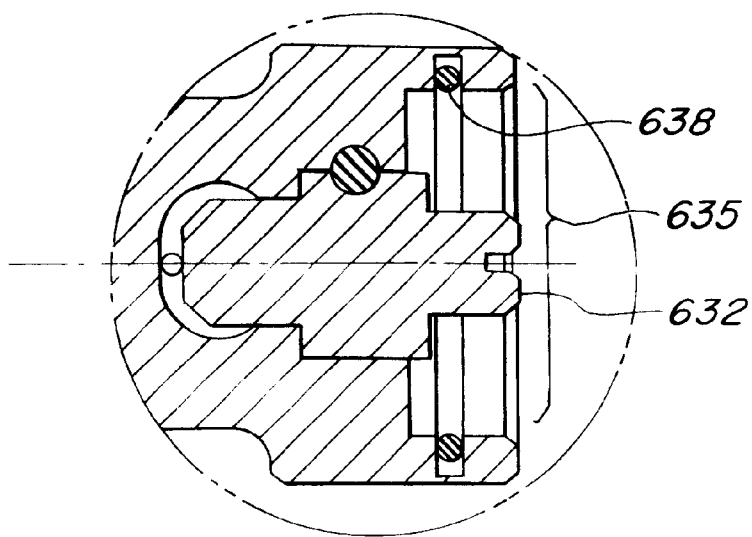

FIGS. 6C and 6D illustrate details of construction of the distal, fastener-securing, end. As shown, the front-most portion is implemented as a box wrench 635 having an en. internal groove securing a circle clip 638 in a position near the distal face, to aid in gripping the external clamping nut fastener. The inner fastener driver insert 630 has a central hexagonal member 632 with a slot or groove running in a plane about the outside of the drive member 632. The slot holds a flex spring 634 that bears outwardly so that set screws are reliably captured on the protruding hexagonal stub of the central member 630. The flex spring 634 has a U-shaped form. The inward-curving distal end reliably and easily fits into the set screw, and the U-shaped proximal end prevents the spring from falling out of the assembly.

FIG. 6E illustrates a spring biased cartridge assembly of a preferred implementation of the tool of FIG. 6A, showing an insert 630 and U-shaped spring 634 in greater detail with the floating central construction. Corresponding parts are numbered similarly to the preceding figures. Both the central stub shaft body 630 and the external wrench body 635 may be made of polymer materials so that, for example, a major portion of the of the tool may be assembled from a small number of injection molded components and the described flex spring and clip elements.

Tool sets of the invention for installing clamp fasteners may also utilize a holder assembly having an essentially axial architecture for aligning the cartridges.

Figure 7A:
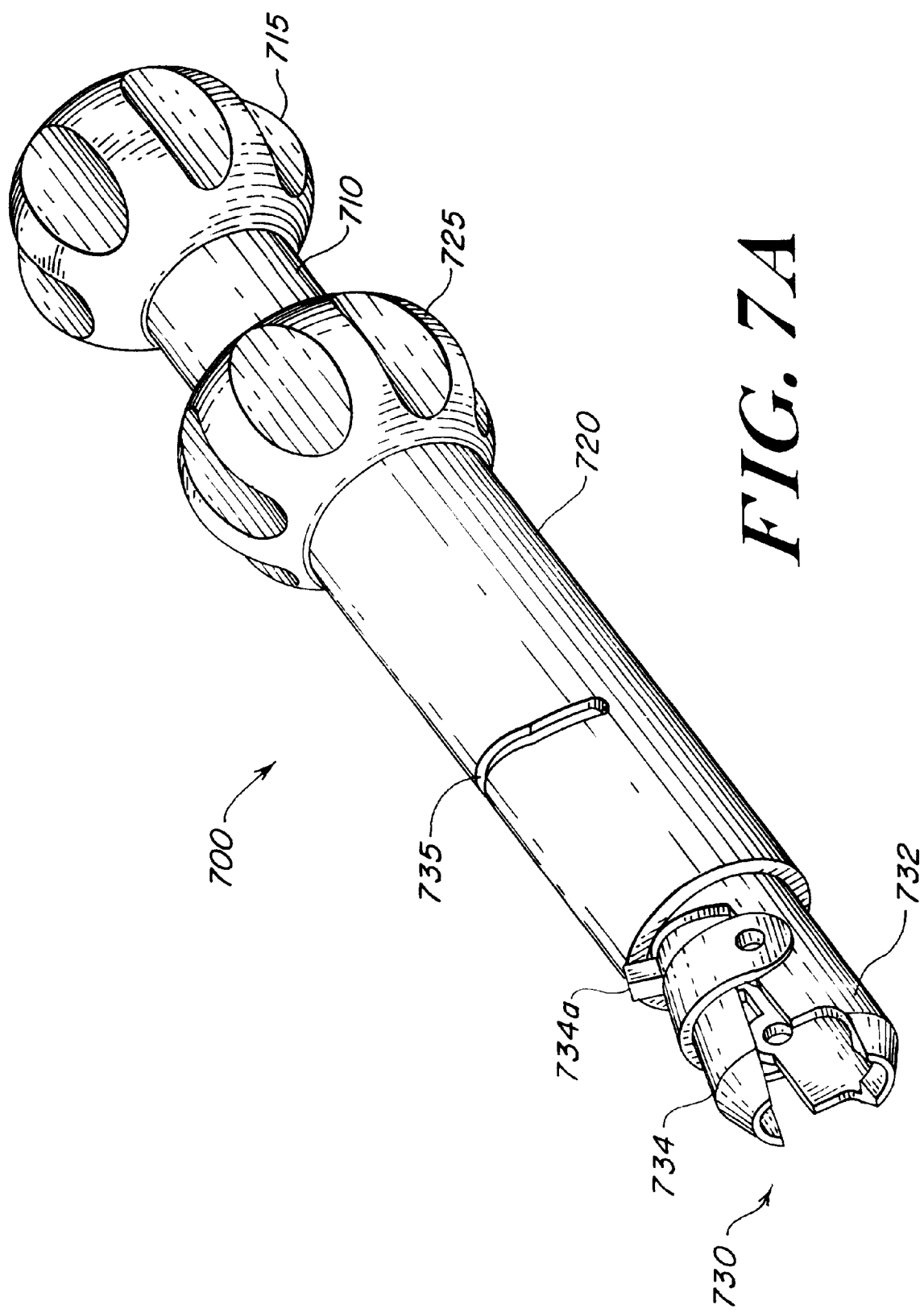
FIGS. 7A–7C schematically illustrate an axially extending cartridge holding and centering assembly of the invention.
Figure 7B:
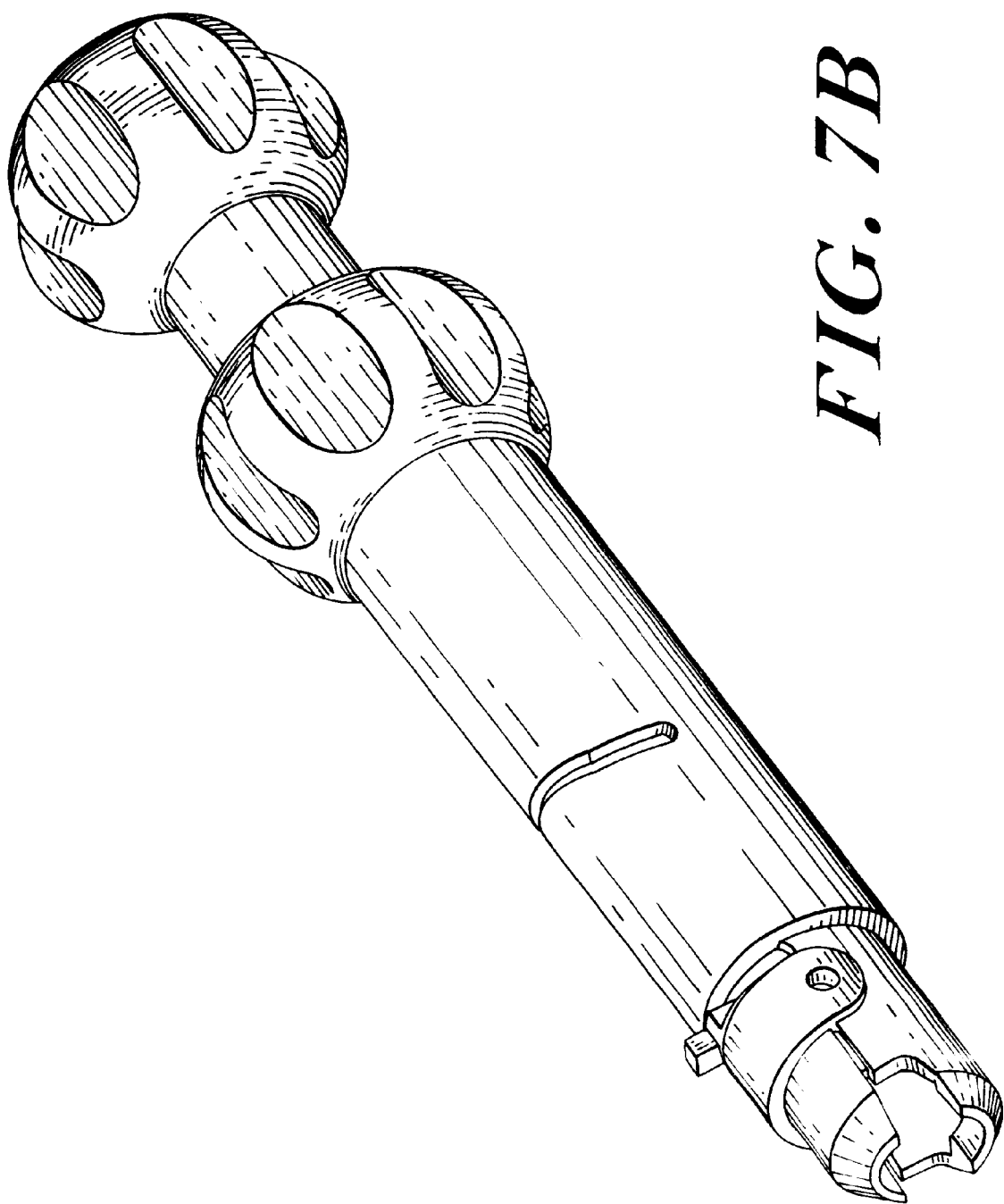
Figure 7C:
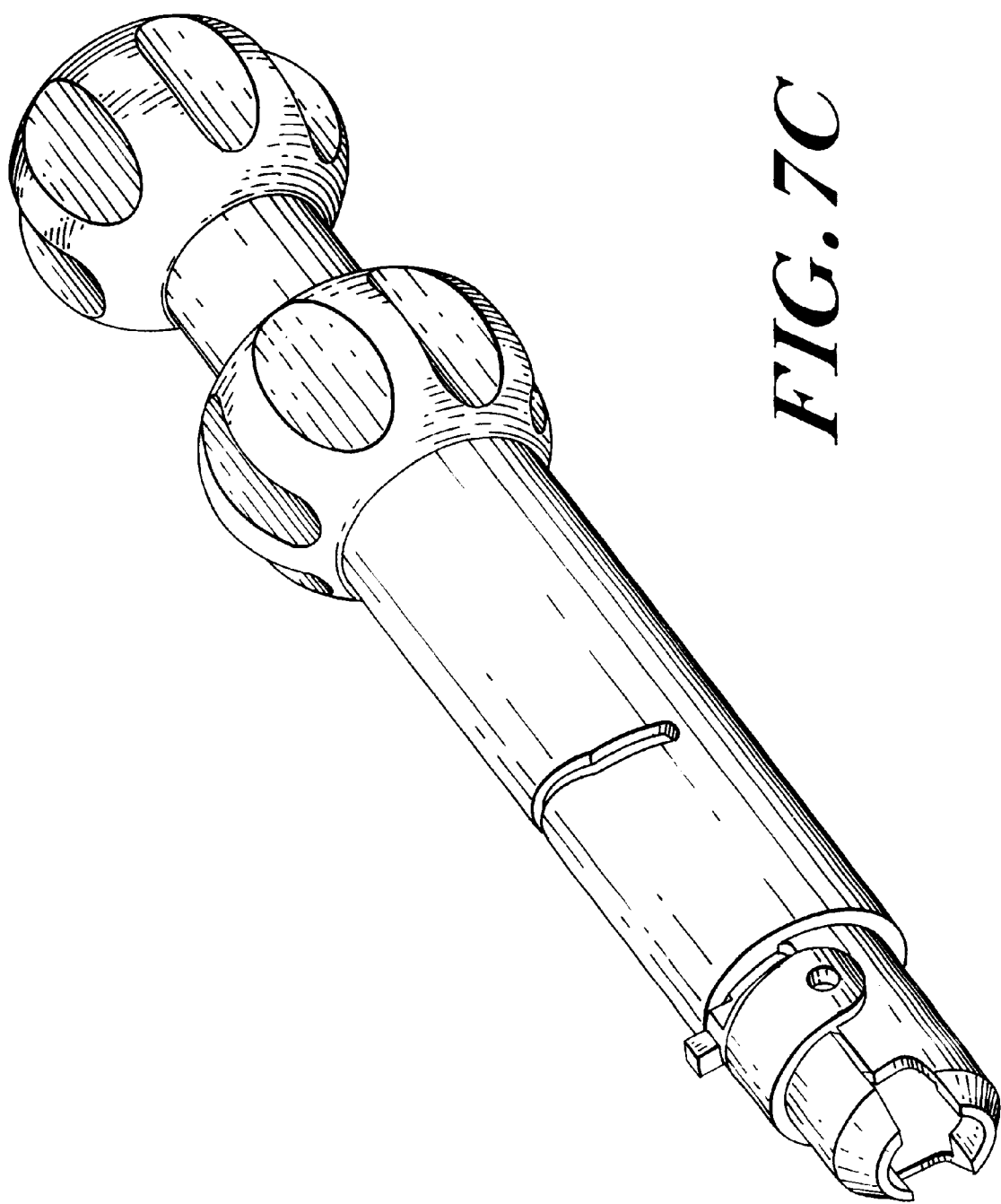

FIGS. 7A–7C schematically illustrate the design for one such holder 700. In this embodiment, an inner cylindrical guide member 710 rotatably fits within an outer guide member 720. Each guide member has a corresponding hand grip portion, 715, 725, respectively, at its proximal end for holding or turning the assembly. The inner member 710 further has a jaw assembly 730 at its distal end that is shaped for clamping onto an anchor head as described above. The jaw assembly 730 includes a fixed jaw 732 that is coaxially concentric with and rigidly integral with the inner cylindrical body 710, and a movable jaw 734 hingedly mounted to the body 710 and opposed to the fixed jaw 732. A radially protruding dog or tab 734a at the distal end of the movable jaw is captured by a closure mechanism (one example of which is shown in FIG. 8A, below) that is carried on the outer member 720 and operates to pivot the jaw open or closed as members 710, 720 rotate with respect to each other. FIG. 7A shows the jaw 730 in an open position, while FIGS. 7B and 7C show the jaw 730 in a semi-closed and a fully-closed position respectively. The assembly may includes guides, stops or detents that define a specific semi-closed position wherein the jaws are only slightly open, e.g., several degrees above the central axis, such that the jaws fit in close alignment on the head of an anchor screw prior to complete closing. As the members 710, 720 are moved to close the jaws, the holder may be rocked or wiggled to exactly center and seat the assembly on the anchor head.

Figure 8B:
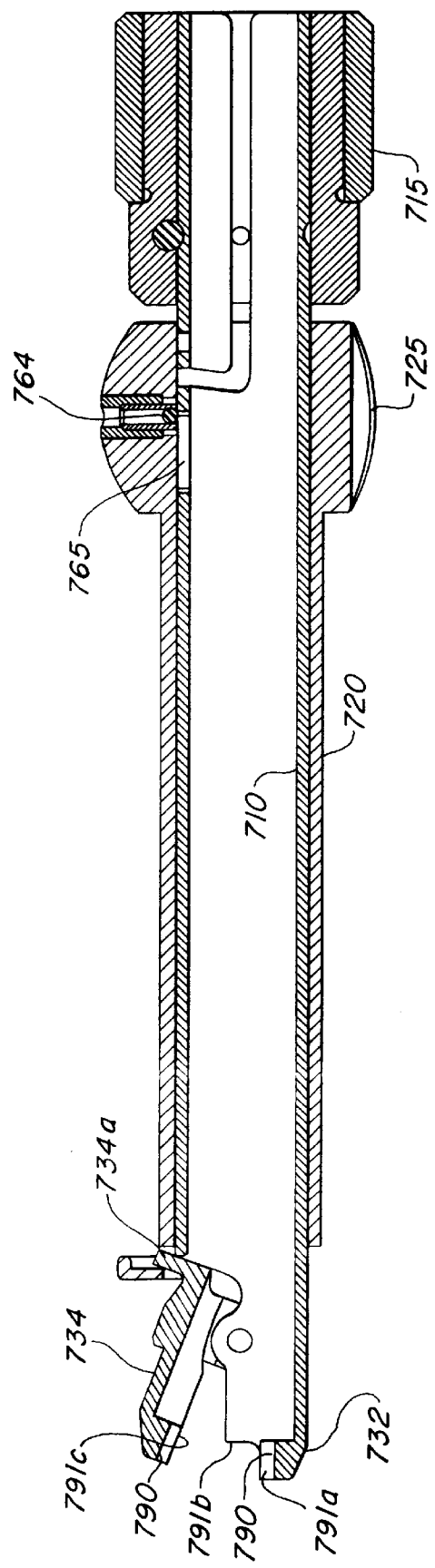
Figure 8C:
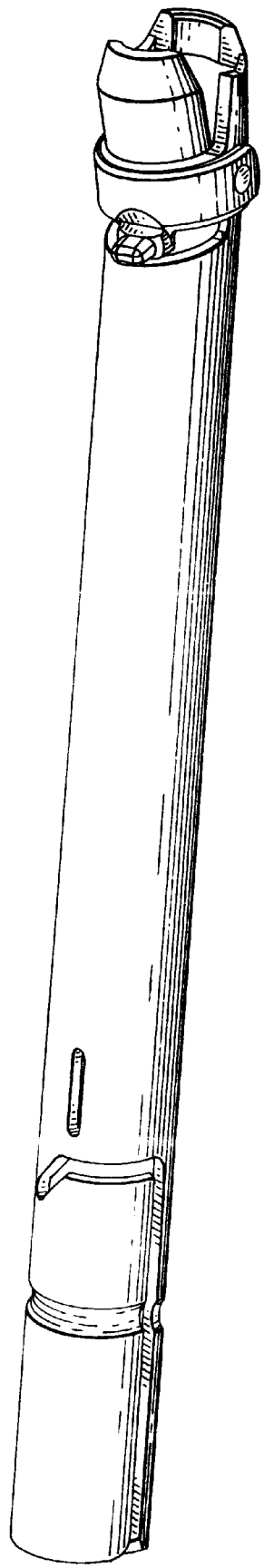

FIGS. 8A–8C illustrate details of one practical embodiment of the axial holder assembly as schematically shown in FIGS. 7A–7C. As shown in the perspective and cross-sectional views, the jaw 730 is actuated by a jaw closure assembly 740 that has a circumferential guide bar 742 by which the tab 734a is captured and is moved axially as the outer guide member 720 is rotated while the inner guide member is held rigid. The axial motion of the outer guide member 720 is controlled, e.g., by a protruding follower 735 (FIG. 7A). In the illustrated embodiment, when the proximal handle is held rigid and the distal handle is rotated fully in a counter clockwise direction, the jaws are in the open position shown in FIG. 7A. The distal handle is then rotated clockwise until the ball plunger 764 crosses the detent groove 765. This detent position can be heard or felt, and it indicates to the surgeon that the jaws 732,734 are open just enough that the cylindrical bore 790 fits over the head of the anchor (e.g., a polyaxial screw or a hook). In this position, the surfaces 791a, 791b, 791c at the tip of the jaw form a channel or yoke that can be used to approximate, that is to push or urge the spinal rod into the head of the anchor. Once the rod is seated, the distal handle is further rotated to fully close the jaws onto the anchor screw or hook. This unique camming action for actuating gripping jaws provides a fast and ergometric mechanism for effectively aligning and attaching the guide assembly. Once attached to the anchor screw head or anchor hook, the cartridge is then introduced into the cylindrical guide to apply the fastener, or the pair of inner and outer fasteners to the anchor screw head.

Advantageously, as shown in FIGS. 8A and 8B, the proximal handle 715 is removably attached to the inner guide, and the jaw actuation mechanism 740 extends only about a partial circumference. Thus when the device is rotated past the fully closed position (with nothing in the jaw), and the handle 715 is detached, the inner tube may be drawn out of the outer tube so that all components are fully exposed for sterilization, reassembly and reuse.

In yet other embodiments, different mechanisms may be utilized to effect jaw movement and locking. The cartridge holder 700 has an internal cylindrical bore sized to closely receive and to axially orient the elongated fastener cartridges or cartridges with extending handle portions as described above. Shorter cartridges may also be used in the guide assembly of FIGS. 7–8, in which case an additional driver, such as an Allen wrench, may be used to access and turn the cartridge.

This completes a description of several basic embodiments and illustrative details for construction fastener cartridges and guides, and systems of the present invention. It will be apparent that features of one embodiment may be employed in others. Thus, for example, the enlarged proximal end of the cartridge illustrated in FIG. 1 may instead be a same-diameter, or a smaller but knurled diameter to permit that cartridge to be used either in a short guide, as a stand-alone installation tool, or with longer cylindrical guides, such as the guides of FIGS. 7 and 8. Furthermore, the floating central driver of the described cartridges may be employed in a cartridge designed to apply only an external (nut) fastener, or only an internal (set screw) fastener. The invention also contemplates cartridge of the invention may be configured to hold and automatically advance and apply a plurality of nuts, advancing each as the preceding one is applied. Furthermore, the cartridges may be equipped not simply with a hand grip or a drive socket at their proximal end, but may have a universal joint socket at that end to allow turning to be accomplished with a separate driver held at odd angles and remote from the surgical site. Such a U-jointed socket is especially advantageous for the occluded sites when operating around the fourth and fifth lumbar vertebrae.

The invention being thus disclosed and illustrative embodiments depicted herein, further variations and modifications of the invention, will occur to those skilled in the art, and all such variations and modifications are considered to be within the scope of the invention, as defined by the claims appended hereto and equivalents thereof.

What is claimed is:

1. A tool for use by a surgeon to apply a fastener to an implanted anchor, wherein the anchor has a head for clamping a rod, cable or other fixation member, said tool comprising an alignment guide having a centering body with a set of distal end jaws adapted to circumferentially grip the anchor head and thereby axially align the centering body with the implanted anchor, and a fastener cartridge rotatably positionable in the centering body for coaxially applying both an inner and an outer screw element to the anchor head without cross threading for clamping the fixation member therein.

2. The tool of claim 1, wherein the alignment guide includes a substantially cylindrical centering body having said distal end jaws, and an elongated handle projecting to a side of said centering body for manipulating the guide in a surgical wound.

3. The tool of claim 1, wherein the alignment guide includes a substantially cylindrical centering body having said distal end jaws, and a substantially cylindrical actuation member telescopically interfitted with the centering body and having an enlarged torque grip for actuating the distal end jaws.

4. The tool of claim 1, wherein the fastener cartridge has a substantially cylindrical body having an outside wall forming a box wrench for externally holding and turning a nut, and further has a shaft centrally mounted in the box wrench for positioning and rotating a clamping screw coaxially with the nut.

5. The tool of claim 1, wherein said box wrench and central shaft extend so as to position the inner and outer fastening elements such that cartridge rotation installs the inner element coaxially with but ahead of the outer element to clamp a linking member to the screw head.

6. The tool of claim 1, wherein the fastener cartridge includes a box wrench disposed around a central driver, and further comprises a spring assembly such that a fastener held in the cartridge floats urging a fastener into alignment as it engages threads of the anchor.

7. A tool for use by a surgeon to clamp to a spinal fixation anchor, wherein the spinal fixation anchor has an anchor head for clamping a rod, cable or other fixation member, said tool including a fastener cartridge having a substantially cylindrical body with an outside wall forming a box wrench for externally holding and turning a nut, said cartridge further having a shaft centrally mounted in the box wrench for positioning and rotating a lock screw coaxially with the nut, said box wrench and central shaft extending so as to position an outer nut and an inner lock screw such that cartridge rotation installs the inner lock screw coaxially with but ahead of the outer nut on the anchor head.

8. The tool of claim 7, wherein the box wrench has an internal circumferential spring for frictionally retaining the nut.

9. The tool of claim 7, wherein the central shaft has a radially biased spring element for retaining the lock screw on the central shaft.

10. The tool of claim 7, wherein the cartridge is configured to retain and apply plural sets of nuts and lock screws to anchor heads.

11. The tool of claim 9, wherein the cartridge receives a stack of nuts and lock screws, each lock screw being centered in a corresponding nut.

12. The tool of claim 7, wherein the box wrench has a floor region centrally offset along the axis of the shaft to position the lock screw ahead of the nut.

13. The tool of claim 7, wherein the cylindrical body has an external hand-grippable region allowing manual rotation of the nut and set screw.

14. The tool of claim 7, further including a bias assembly such that a fastener floats axially in the fastener cartridge so as to orient the fastener to engage threads of the anchor head.

15. A tool for use by a surgeon to affix clamping fasteners to a spinal anchor head, wherein the spinal anchor head is anchored to hard tissue and includes an opening for clamping a rod or other linking member, said tool comprising a fastener cartridge including a substantially cylindrical body having an outer wall forming a box wrench for externally holding and turning a nut, and a shaft centrally mounted in the cylindrical body for positioning and rotating a clamping screw coaxially with the nut, said box wrench and central shaft extending so as to position an outer nut and an inner lock screw such that cartridge rotation applies the inner lock screw coaxially with but ahead of the outer nut to fix the linking member in the anchor head.

16. The tool of claim 15, further comprising a holder forming a kit, wherein the holder comprises a distal end jaw assembly having plural jaw segments adapted to clamp to the anchor head and align a cartridge body along a fastener installation axis, and a handle assembly having a handgrip portion remote from said distal end jaw, said handgrip portion being configured to position the distal end jaw assembly on the anchor head in a surgical wound to provide a guide for the fastener cartridge and to release the segments and remove the holder after installation of the clamping fasteners.

17. The tool of claim 15, wherein the box wrench has a floor region centrally offset 1 along the axis of the shaft to position the lock screw ahead of the nut.

18. The tool of claim 15, wherein the box wrench is spring biased along an axial direction with respect to the shaft to position the lock screw ahead of the nut.

19. A tool for use by a surgeon to clamp a linking member in a spinal anchor, said tool comprising a cartridge adapted to hold a set screw and a nut, wherein the cartridge includes a driver for driving the set screw, and a wrench socket for turning the nut, the driver and wrench socket being arranged concentrically in said turning body and the driver being axially biased to install a set screw on a spinal anchor in coordination with the nut by rotation of the cartridge.

20. The tool of claim 19, wherein the cartridge comprises a spring mechanism for effecting axial bias.

21. The tool of claim 19, wherein the cartridge comprises a spring bias mechanism for securing and advancing plural pairs of concentric fasteners.

22. The tool of claim 19, wherein the cartridge further comprises an elongated handle extending along an installation axis for manually turning the tool to install fasteners.

23. A tool for use by a surgeon as a guide to affix clamping fasteners to an anchor head, wherein the anchor head is anchored to hard tissue and includes an opening for clamping a rod or other linking member, said tool comprising a distal end jaw assembly having plural jaw segments adapted to clamp to the anchor head and being coupled to a guide body such that the guide body aligns along a fastener installation axis when so clamped, and a handle assembly having a handgrip portion remote from said distal end jaw, said handgrip portion being configured to position the distal end jaw assembly on the anchor head in a surgical wound to provide a guide for the fastener cartridge and to actuate the jaw assembly to clamp the anchor head.

24. The tool of claim 23, wherein the guide body includes a substantially cylindrical guide portion.

25. The tool of claim 24, further comprising a fastener cartridge forming a set, wherein the cartridge fits concentrically in said cylindrical portion.

26. The tool of claim 25, wherein said fastener cartridge comprises a substantially cylindrical body having an outer wall forming a box wrench for externally holding and turning a nut, and a shaft centrally mounted in the cylindrical body for positioning and rotating a lock screw coaxially with the nut, said box wrench and central shaft coordinating application of the nut and lock screw to apply them to the anchor head without cross threading.

* * * * *